(12) United States Patent
Knoplioch et al.

(10) Patent No.: US 6,445,762 B1
(45) Date of Patent: Sep. 3, 2002

(54) METHODS AND APPARATUS FOR DEFINING REGIONS OF INTEREST

(75) Inventors: Jerome Francois Knoplioch, Neuilly sur Seine; Gilles R. Moris, Boulogne-Billancourt, both of (FR); James Donald Markvicka, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/683,135

(22) Filed: Nov. 26, 2001

(51) Int. Cl.$^7$ .................................................. A61B 6/03
(52) U.S. Cl. ............................ 378/8; 382/128; 378/901
(58) Field of Search ................................ 378/4, 8, 901; 382/131, 128, 173

(56) References Cited

U.S. PATENT DOCUMENTS 6,123,669 A * 9/2000 Kanda .......................... 128/916
6,396,939 B1 * 5/2002 Hu et al. ...................... 382/128

* cited by examiner

*Primary Examiner*—David V. Bruce
(74) *Attorney, Agent, or Firm*—Carl B. Horton, Esq.; Armstrong Teasdale LLP

(57) ABSTRACT

A method for interactively creating a region of interest of a reconstructed image includes defining a thickness value, defining a polygon, and defining a 3D projection geometry. The method also includes defining a vector perpendicular to a line of sight which is defined by the 3D projection geometry, swiping the vector along the polygon to create a surface of interest, and displaying three dimensionally a plurality of points wherein a distance from the points to the created surface along the line of sight is approximately the defined thickness value or less.

28 Claims, 2 Drawing Sheets

METHODS AND APPARATUS FOR DEFINING REGIONS OF INTEREST

BACKGROUND OF INVENTION

This invention relates generally to methods and apparatus for interactive defining regions of interest for creating computed tomographic (CT) images, magnetic resonance (MR) images, and x-ray (XR) images, and more particularly to methods and apparatus for defining such regions around tortuous structures.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

CT, MR and XR routinely produce 3D data sets. Analyzing tortuous structures, such as airways, vessels, ducts or nerves is one of the major applications of these devices. Known methods and apparatus for accomplishing such analysis use multiple oblique slices to analyze local segments of these structures. The multiple oblique slice views provide clear, undistorted pictures of short sections of tortuous structures, but rarely encompass their full length.

Curved reformation images also provide synthetic views of tortuous structures, and advantageously capture the whole length of these objects. Thus, curved reformation images are well suited to analysis of such structures. True 3D length measurements along an axis of a tortuous structure can be obtained from these views, and measurements from these views are sufficiently close to the real anatomy in many cases. However, those synthetic views are limited to a single voxel depth and therefore contain less information about the anatomy than a full 3D view.

In one known technique, curved reformation images are generated by sampling values along a curve at equidistant points to generate lines, and then translating the curve using a sampling vector to generate the next image line (i.e., along any 2D orientation). By representing the points in a polar coordinate system, with all of the points in the upper two quadrants of the coordinate system, a cubic spline algorithm is applied to a redefined set of points, thereby generating a series of functions that best approximates a desired curve. A conversion is then done to generate screen coordinates for selecting pixel values to display. Also, additional curves equidistant from an original curve are generated to produce additional views of the scanned structure. The calculation of these additional curves also uses a polar coordinate representation of cubic spline coefficients for the initial curve. These coefficients are used to determine intermediate data points at which a uniform length perpendicular is constructed. New data points equidistant from the initial curve are calculated by traversing each perpendicular a desired length.

Such known techniques and systems do not provide for user-friendly interactive creation of regions of interest well-suited to the display of tortuous structures. For example, in some known implementations, a curve is translated interactively but artifacts are created in the case of tortuous structures because the sampling curve may be outside of the object. These artifacts look like pseudo-stenoses.

To display some features, for example, bifurcations, local stenoses, and calcifications, one must manually redefine a sampling vector. This process is time consuming. Also, it is difficult to adjust the display to depict selected features. Also, the display assumes that the target features are known when the sampling vector is selected. Therefore, this known method is not practical for medical review because the possible lesions are not known ahead of time.

SUMMARY OF INVENTION

In one aspect, a method for interactively creating a region of interest of a reconstructed image is provided. The method includes defining a thickness value, defining a polygon, and defining a 3D projection geometry. The method also includes defining a vector perpendicular to a line of sight which is defined by the 3D projection geometry, swiping the vector along the polygon to create a surface of interest, and displaying three dimensionally a plurality of points wherein a distance from the points to the created surface along the line of sight is approximately the defined thickness value or less.

In another aspect, a method for interactively creating a region of interest of a reconstructed image is provided. The method includes defining a thickness value, defining a polygon, and defining a 3D projection geometry. The method also includes defining a vector perpendicular to a line of sight which is defined by the 3D projection geometry, swiping the vector along the polygon to define a surface, and swiping the surface along the line of sight to create a volume of interest. The method also includes intersecting the volume of interest with a three dimension data set, and three dimensionally displaying the intersection.

In a further aspect, a scanning system is provided. The scanning system includes a radiation source, a radiation detector positioned to receive radiation emitted from the source, and a processor operationally coupled to the detector. The processor is configured to receive a thickness value, define a polygon, and receive a 3D projection geometry definition. The processor is further configured to define a vector perpendicular to a line of sight which is defined by the 3D projection geometry, swipe the vector along the polygon to create a surface of interest, and display three dimensionally a plurality of points wherein a distance from the points to the created surface along the line of sight is approximately the defined thickness value or less.

In still a further aspect, a scanning system includes a radiation source, a radiation detector positioned to receive radiation emitted from the source, and a processor operationally coupled to the detector, wherein the processor is configured to receive a thickness value, and define a polygon. The processor is also configured to define a 3D projection geometry, define a vector perpendicular to a line of sight which is defined by the 3D projection geometry, and swipe the vector along the polygon to define a surface. The processor is also configured to swipe the surface along the line of sight to create a volume of interest, intersect the volume of interest with a three dimension data set, and display three dimensionally the intersection.

DETAILED DESCRIPTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Figure 1:
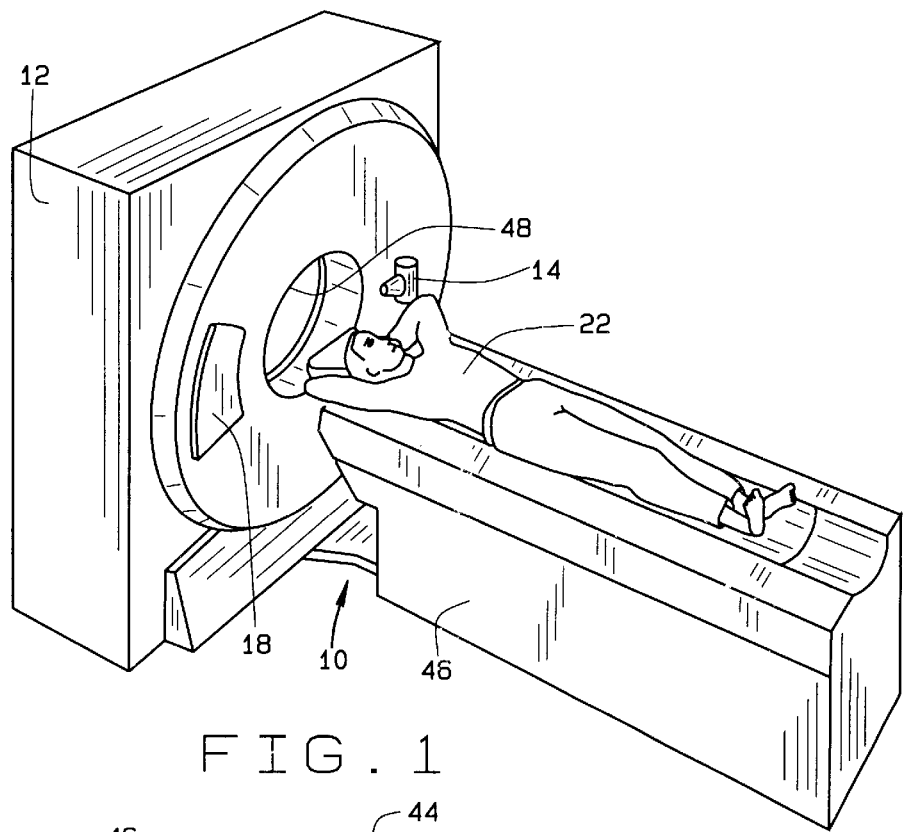
FIG. 1 is a pictorial view of a CT imaging system.
Figure 2:
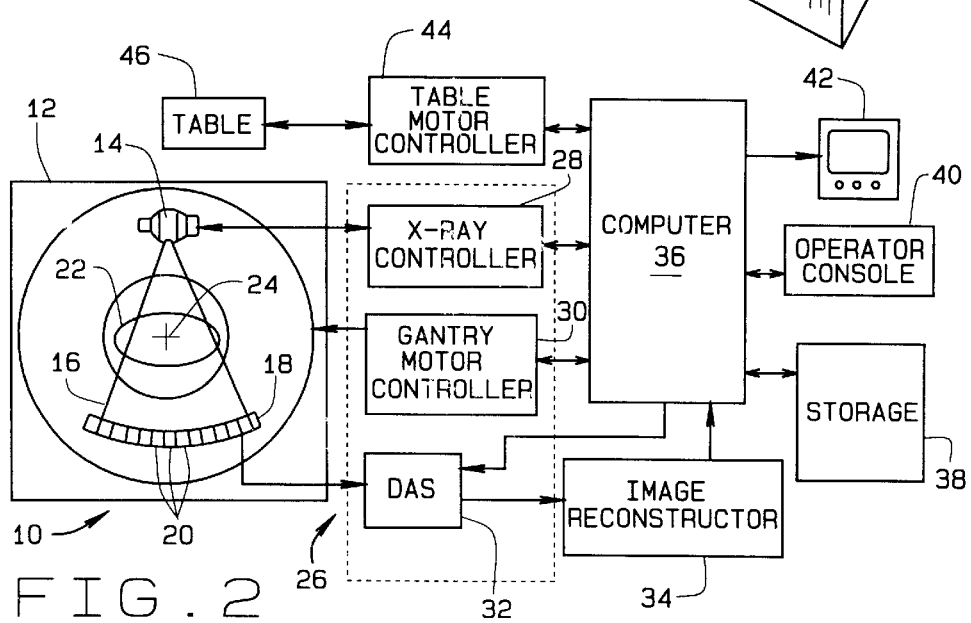
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

One embodiment of the present invention makes use of software or firmware running on computer 36 along with console 40 and display 42 to interactively rotate a sampling surface so as to quickly display relevant images in a limited amount of time. A mouse or other pointing device (not shown) can also be provided to facilitate entry of data and/or image locations. A full volumetric analysis of a portion of patient 22 can thus be performed in a user-friendly way. Other embodiments utilize a general purpose computer or workstation having a memory (i.e., short-term or long-term storage) and/or printing capability for storing or printing images. Suitable memory devices are well known and include, but are not limited to, RAM, diskettes, hard drives and optical media. Embodiments using such stand-alone computers or workstations receive data from which images are reconstructed from CT imaging system 10 via conventional electronic storage media (not shown) or via a conventional communication link (not shown).

Figure 3:
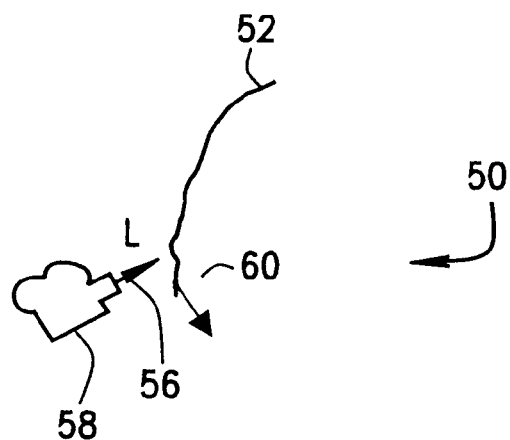
FIG. 3 illustrates an image that is selected for display on the display shown in FIGS. 1 and 2.
Figure 4:
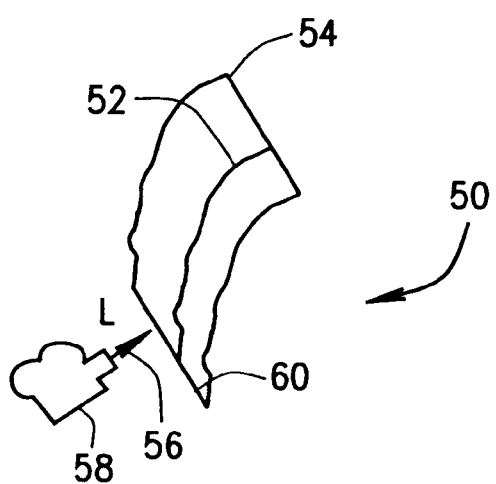
FIG. 4 illustrates an image that is selected for display on the display shown in FIGS. 1 and 2.

In one embodiment of the present invention, a scan is performed on a volume of patient 22, resulting in the collection of a plurality of slices of image data. Referring to FIGS. 3 and 4, one image 50 is selected for display on display 42. A polygon 52 is then defined that approximates a centerline of a structure of interest 54. This definition is performed, for example, by using automated methods that track the centerline or by using data manually input by a user. For example, manual input is obtained by drawing on any view of a volume containing the structure of interest with a mouse or other pointing device. A thickness value (T) and a 3D projection geometry are defined. The 3D projection geometry definition includes a choice of using a rotation matrix or not. A vector 56 projecting along the normal to the screen is labeled L (for Line of sight of a camera 58).

A vector 60 is selected perpendicular to L. In one embodiment, vector 60 is a horizontal screen axis. In another embodiment, vector 60 is a vertical axis screen axis. Alternatively, vector 60 is the vector product of L and a main axis of polygon 52, wherein the main axis is computed using a linear regression technique. By swiping vector 60 along polygon 52, a surface (S) is generated, and by swiping the surface S along the line of sight L, a volume of interest is generated. The volume is displayed by three dimensionally displaying a plurality of points wherein a distance from the points to the created surface along the line of sight is approximately the defined thickness value or less. In an exemplary embodiment, the distance from the displayed points to the created surface along the line of sight is the defined thickness value or less. Additionally, in one embodiment the smaller volume (i.e., the displayed volume) is not explicitly created, rather, the determining if the distance is equal or less than the defined thickness is performed "on-the-fly" during a display. In other words, in this case, the whole volume is traversed or used during display and if a point is determined during this traversal as not meeting the above test regarding distance, then that point is not displayed.

Also a reference plane (R) for the screen can be used after the volume is generated to facilitate displaying the volume. The reference plane is any plane parallel to the screen. For example, a pair of 2D buffers (b and B) are created and letting D represent the distance from of a point to R along L the buffers are created such that $b(x,y) \leq D \leq B(x,y)$. Additionally, by defining a variable thickness, the thickness at least partially varies along a length of polygon 52. In one embodiment, after swiping the surface along the line of sight to create a volume of interest, the volume of interest in intersected with a three dimension data set and the intersection is three dimensionally displayed. Additionally, for each point on a screen displaying the image, a plurality of coordinates of segments are generated, wherein the segments for a particular point are formed by intersecting the line of sight at that particular point with the defined volume to define a surface along the line of sight, wherein the surface is constrained by the defined thickness. In an exemplary embodiment, the coordinates are stored in a plurality of pairs of buffers, wherein each point has a corresponding pair of buffers such as b(x,y) and B(x,y), and for each point on the screen displaying the image, a plurality of coordinates for a segment are generated, wherein the segment for a particular point is the closest segment to camera 58 and wherein the segment is formed by intersecting the line of sight at that particular point with the defined volume to define a surface along the line of sight, and wherein the surface is constrained by the defined thickness.

Accordingly, a user friendly analysis of tortuous structures can quickly be performed by producing views that depict the structures in their entirety. Additionally, an operator can quickly locate and display features such as local stenoses, aneurysms, calcifications, bifurcations, and other features in a natural relation to the overall structure of the structure of interest. Additionally, by defining volumes of interest around anatomical features and excluding unnecessary voxels, a reduction in 3D rendering time is facilitated.

Although the methods described herein are in the context of a computed tomography system, the methods are not limited to practice with computed tomography systems and can be utilized in many different imaging modalities. For example, the methods can be used in connection with x-ray, magnetic resonance, positron emission tomography, ultrasound, and other imaging modalities.

While the invention has been described in terms of various specific embodiments, those skilled in the art will recognize that the invention can be practiced with modification within the spirit and scope of the claims.

What is claimed is:

1. A method for interactively creating a region of interest of a reconstructed image comprising:
    defining a thickness value;
    defining a polygon;
    defining a 3D projection geometry;
    defining a vector perpendicular to a line of sight which is defined by the 3D projection geometry;
    swiping the vector along the polygon to create a surface of interest; and
    displaying three dimensionally a plurality of points wherein a distance from the points to the created surface along the line of sight is approximately the defined thickness value or less.

2. A method in accordance with claim 1 wherein displaying three dimensionally a plurality of points comprises displaying three dimensionally a plurality of points wherein the distance from the points to the created surface along the line of sight is the defined thickness value or less.

3. A method in accordance with claim 1 wherein defining a polygon comprises automatically generating a polygon utilizing a centerline tracking algorithm.

4. A method in accordance with claim 1 wherein defining a vector comprises defining a vector perpendicular to a linear regression determined major axis of the polygon.

5. A method in accordance with claim 1 wherein defining a thickness value comprises defining a variable thickness such that the thickness at least partially varies along a length of the polygon.

6. A method for interactively creating a region of interest of a reconstructed image comprising:
    defining a thickness value;
    defining a polygon;
    defining a 3D projection geometry;
    defining a vector perpendicular to a line of sight which is defined by the 3D projection geometry;
    swiping the vector along the polygon to define a surface;
    swiping the surface along the line of sight to create a volume of interest;
    intersecting the volume of interest with a three dimension data set; and
    three dimensionally displaying the intersection.

7. A method in accordance with claim 6 wherein defining a polygon comprises automatically generating a polygon utilizing a centerline tracking algorithm.

8. A method in accordance with claim 6 wherein defining a vector comprises defining a vector perpendicular to a linear regression determined major axis of the polygon.

9. A method in accordance with claim 6 wherein defining a thickness value comprises defining a variable thickness such that the thickness at least partially varies along a length of the polygon.

10. A method in accordance with claim 6 wherein defining a 3D projection geometry comprises defining a reference plane parallel to a screen displaying the image.

11. A method in accordance claim 10 wherein swiping the surface along the line of sight to create a volume of interest comprises:
    generating, for each point on a screen displaying the image, a plurality of coordinates of segments, wherein the segments for a particular point are formed by intersecting the line of sight at that particular point with the defined volume to define a surface along the line of sight, wherein the surface is constrained by the defined thickness; and
    storing the coordinates in a plurality of pairs of buffers, wherein each point has a corresponding pair of buffers.

12. A method in accordance with claim 11 wherein three dimensionally displaying the intersection comprises three dimensionally displaying a plurality of points for which the distance from each particular point to the reference plane is within the bounds of that particular point's corresponding pair of buffers.

13. A method in accordance claim 10 wherein swiping the surface along the line of sight to create a volume of interest comprises:
    generating, for each point on a screen displaying the image, a plurality of coordinates for a segment, wherein the segment for a particular point is the closest segment to a camera and wherein the segment is formed by intersecting the line of sight at that particular point with the defined volume to define a surface along the line of sight, wherein the surface is constrained by the defined thickness; and
    storing the coordinates in a plurality of pairs of buffers, wherein each point has a corresponding pair of buffers.

14. A method in accordance with claim 11 wherein three dimensionally displaying the intersection comprises three dimensionally displaying a plurality of points for which the distance from each particular point to the reference plane is within the bounds of that particular point's corresponding pair of buffers.

15. A scanning system comprising:
a radiation source;
a radiation detector positioned to receive radiation emitted from said source; and
a processor operationally coupled to said detector, said processor configured to:
receive a thickness value;
define a polygon;
receive a 3D projection geometry definition; define a vector perpendicular to a line of sight which is defined by the 3D projection geometry;
swipe the vector along the polygon to create a surface of interest; and display three dimensionally a plurality of points wherein a distance from the points to the created surface along the line of sight is approximately the defined thickness value or less.

16. A system in accordance-with claim 15 wherein said processor is further configured to generate a polygon utilizing a centerline tracking algorithm.

17. A system in accordance with claim 15 wherein said processor is further configured to define a vector perpendicular to a linear regression determined major axis of the polygon.

18. A system in accordance with claim 15 wherein said detector comprises a computed tomography (CT) detector.

19. A system in accordance with claim 15 wherein said detector comprises a magnetic resonance (MR) detector.

20. A system in accordance with claim 15 wherein said detector comprises an x-ray (XR) detector.

21. A scanning system comprising:
a radiation source;
a radiation detector positioned to receive radiation emitted from said source; and
a processor operationally coupled to said detector, said processor configured to:
receive a thickness value;
define a polygon;
define a 3D projection geometry;
define a vector perpendicular to a line of sight which is defined by the 3D projection geometry;
swipe the vector along the polygon to define a surface;
swipe the surface along the line of sight to create a volume of interest;
intersect the volume of interest with a three dimension data set; and
display three dimensionally the intersection.

22. A system in accordance with claim 21 wherein said processor is further configured to generate a polygon utilizing a centerline tracking algorithm.

23. A system in accordance with claim 22 wherein said processor is further configured to define a vector perpendicular to a linear regression determined major axis of the polygon.

24. A system in accordance with claim 21 wherein said detector comprises a computed tomography (CT) detector.

25. A system in accordance with claim 22 wherein said detector comprises a magnetic resonance (MR) detector.

26. A system in accordance with claim 23 wherein said detector comprises an x-ray (XR) detector.

27. A system in accordance with claim 21 wherein to display three dimensionally the intersection, said processor is further configured to display a plurality of points for which the distance from each particular point to a reference plane is within the bounds of that particular point's corresponding pair of buffers.

28. A system in accordance with claim 21 wherein said processor is further configured to generate, for each point on a screen displaying the image, a plurality of coordinates for a segment, wherein the segment for a particular point is the closest segment to a camera and wherein the segment is formed by intersecting the line of sight at that particular point with the created volume to define a surface along the line of sight, wherein the surface is constrained by the defined thickness; and
storing the coordinates in a plurality of pair of buffers, wherein each point has a corresponding pair of buffers.

* * * * *